(12) United States Patent
Erickson et al.

(10) Patent No.: US 7,828,783 B2
(45) Date of Patent: Nov. 9, 2010

(54) ABSORBENT ARTICLE HAVING AN UMBILICAL NOTCH CUT

(75) Inventors: Gregory John Erickson, Blue Ash, OH (US); Jason Robert Eddy, Liberty Township, OH (US); John Ferrer, Mason, OH (US); Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/020,042

(22) Filed: Jan. 25, 2008

(65) Prior Publication Data

US 2008/0119809 A1 May 22, 2008

Related U.S. Application Data

(62) Division of application No. 11/039,950, filed on Jan. 20, 2005, now Pat. No. 7,361,167.

(51) Int. Cl.
*A61F 13/15* (2006.01)

(52) U.S. Cl. .................... 604/385.09; 604/385.01; D24/126

(58) Field of Classification Search ............ 604/385.01, 604/385.09; D24/126
See application file for complete search history.

(56) References Cited

U.S. PATENT DOCUMENTS

| | | | |
|---|---|---|---|
| 2,252,988 A | 8/1941 | Segall | |
| D215,642 S | 10/1969 | Lofgren | |
| 4,230,113 A | 10/1980 | Mehta | |
| 4,675,015 A | 6/1987 | Brown | |
| 4,769,023 A | 9/1988 | Goebel et al. | |
| 4,940,464 A | 7/1990 | Van Gompel et al. | |
| D311,582 S | 10/1990 | Gilchrist | |
| 5,092,861 A | 3/1992 | Nomura et al. | |
| D334,978 S | 4/1993 | Rutherford | |
| 5,246,433 A | 9/1993 | Hasse et al. | |
| D341,422 S | 11/1993 | Cosentino | |
| 5,569,234 A | 10/1996 | Buell et al. | |
| 5,643,242 A | 7/1997 | LaVon et al. | |
| D403,402 S | 12/1998 | Dreier et al. | |
| 5,897,545 A | 4/1999 | Kline et al. | |
| 5,957,908 A | 9/1999 | Kline et al. | |
| 6,120,487 A | 9/2000 | Ashton | |

(Continued)

FOREIGN PATENT DOCUMENTS

DE   20216466 U1   2/2003

(Continued)

*Primary Examiner*—Jacqueline Stephens
(74) *Attorney, Agent, or Firm*—Charles R. Ware

(57) ABSTRACT

A disposable absorbent article having a non-linear notch cut without the presence of a significantly laterally extending resulting piece. The resulting absorbent article having a front end edge and a back end edge which are complementary. The front end edge having at least three tangential points ($a_1$, $a_2$, b). Tangential point b is longitudinally inboard of $a_1$ and $a_2$. The back end edge having at least three tangential points ($x_1$, $x_2$, y), wherein y is longitudinally outboard of $x_1$ and $x_2$. The absorbent article being longitudinally folded about a first fold line. The first fold line may be drawn between points $a_2$ and $x_2$. The absorbent article being longitudinally folded about a second fold line, said second fold line may be drawn between points $a_1$ and $x_1$.

11 Claims, 9 Drawing Sheets

U.S. PATENT DOCUMENTS

| | | |
|---|---|---|
| 6,120,489 A | 9/2000 | Johnson et al. |
| D452,315 S | 12/2001 | Coates |
| 6,635,135 B2 | 10/2003 | Kuen et al. |
| 6,652,696 B2 | 11/2003 | Kuen et al. |
| 6,979,380 B2 | 12/2005 | Thorson et al. |
| 2003/0233082 A1 | 12/2003 | Kline et al. |

FOREIGN PATENT DOCUMENTS

| | | |
|---|---|---|
| DE | 10348995 A1 | 5/2004 |
| JP | 62-136505 A2 | 6/1987 |
| JP | 62-199807 A2 | 9/1987 |

ABSORBENT ARTICLE HAVING AN UMBILICAL NOTCH CUT

CROSS REFERENCE TO RELATED APPLICATION

This application is a divisional of U.S. application Ser. No. 11/039,950, filed Jan. 20, 2005, now U.S. Pat. No. 7,361,167 the substance of which is incorporated herein by reference.

FIELD OF THE INVENTION

This invention relates to absorbent articles which are particularly adapted to newborn infants. More specifically, this invention relates to diapers having a U-notched cut without the presence of a significantly laterally extending resulting piece that may create a safety risk.

BACKGROUND OF THE INVENTION

Newborn infants are exceptionally prone to inflammation, infection and colonization of bacteria at the umbilicus as the residual, freshly cut umbilical cord offers an inviting site for bacterial invasion and frictional irritation by the overlying diaper. The rubbing movement of the conventional diaper on an umbilicus which is still raw, as the infant squirms, kicks and moves, often produces a sore place which causes the infant to be quite fretful. The umbilical area is noticeably reddish and inflamed. Also, the overlying diaper can serve as a carrier of bacteria to the unhealed, cut cord and bring about an infection.

Due to the aforementioned reasons, conventional diapers which are particularly adapted for newborns are often constructed with an opening that is located centrally along the width of the end edge of the front panel of the diaper. Said opening is commonly referred to as a U-notch, V-notch or non-linear notch. In the creation of said non-linear notch, a non-linear cutting device is used. More specifically, individual diapers are often made from a plurality of continuous web materials that are subsequently cut into discrete articles (i.e., diapers). During said conventional non-linear notch cuts, however, the diaper often has a significantly laterally extending resulting piece that may create a safety risk. What is needed is a diaper/cut design and process that provides a non-linear notch cut without the presence of a significantly laterally extending resulting piece.

SUMMARY OF THE INVENTION

A disposable absorbent article having a longitudinal axis and a lateral axis. The absorbent article further having a front end edge and a back end edge which are complementary in shape and are formed by a non-linear notch cut; said front end edge having at least three tangential points ($a_1$, $a_2$, b). Tangential point b is longitudinally inboard of $a_1$ and $a_2$. The front end edge having at least two edge points ($c_1$, $c_2$), wherein:

(i) $c_1$ and $c_2$ are longitudinally inboard of $a_1$ and $a_2$, and (ii) $c_1$ and $c_2$ are longitudinally equal or outboard of b.

The front end edge having a contour segment from said point $a_1$ to said point $c_1$ which is a mirror image of a contour segment from said point $a_1$ to said point b. The said front end edge having a path length measured along said contour segment from point $a_1$ to point $c_1$ which is less than or equal to the path length measured along said contour segment from point $a_1$ to point b.

The back end edge having at least three tangential points ($x_1$, $x_2$, y), wherein y is longitudinally outboard of $x_1$ and $x_2$. The said back end edge having at least two edge points ($z_1$, $z_2$), wherein:

(i) $z_1$ and $z_2$ are longitudinally outboard of $x_1$ and $x_2$, and (ii) $z_1$ and $z_2$ are longitudinally equal or inboard of y.

The back end edge has a contour segment from said point $x_1$ to said point $z_1$ which is a mirror image of a contour segment from said point $x_1$ to said point y. The back end edge has a path length measured along said contour segment from point $x_1$ to point $z_1$ which is less than or equal to the path length measured along said contour segment from point $x_1$ to point y.

The absorbent article being longitudinally folded about a first fold line. The first fold line may be drawn between points $a_2$ and $x_2$. The absorbent article being longitudinally folded about a second fold line, said second fold line may be drawn between points $a_1$ and $x_1$.

Further, the absorbent article may have a longitudinal distance, d, which is measured between said tangential point b and said tangential point $a_1$, wherein the longitudinal distance being from about 5 mm to about 25 mm, preferably 10 mm.

Further, the absorbent article may have a lateral distance, f, which is measured between said fold lines, wherein the lateral distance being from about 80 mm to about 100 mm, preferably 90 mm.

Further, the disposable absorbent article may be constructed as an open diaper or pant.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. None of the drawings are necessarily to scale.

DETAILED DESCRIPTION OF THE INVENTION

Definitions

Figure 1:
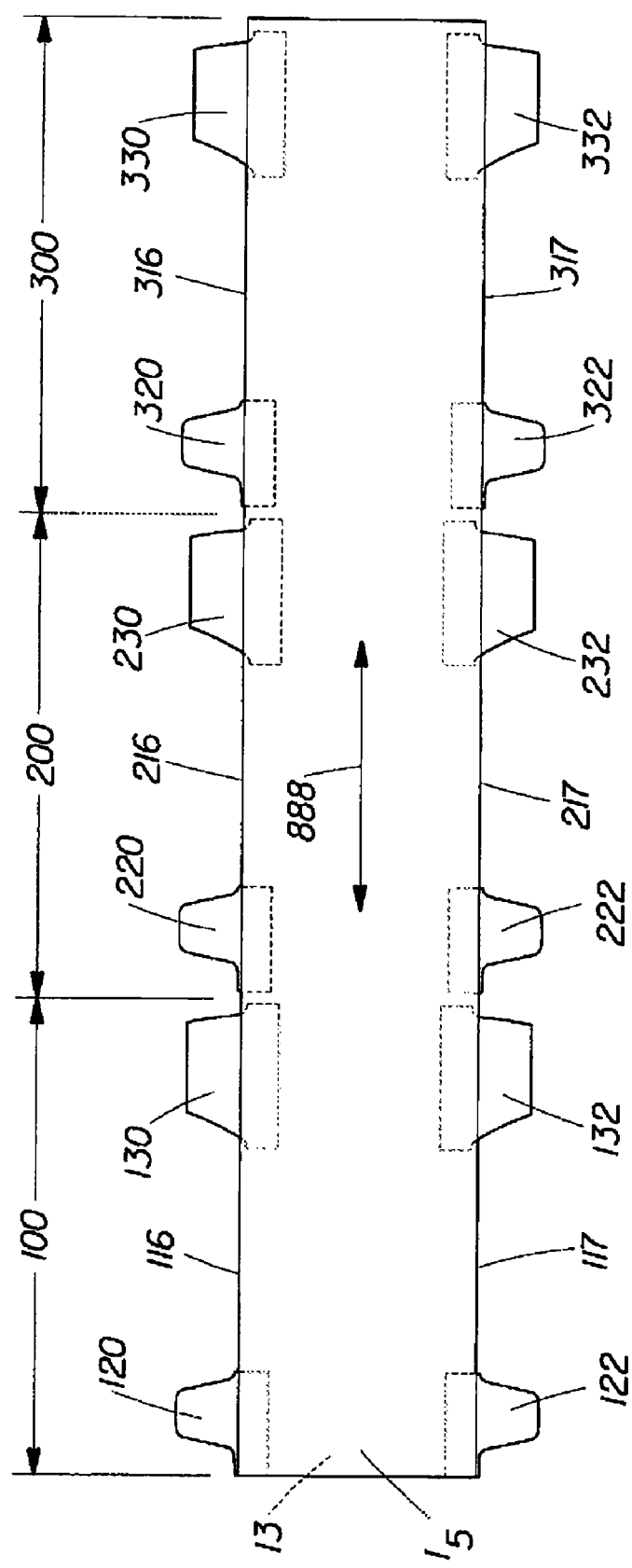
FIG. 1 is a schematic, top view of continuous webs of materials having ears joined thereto, said webs being converted for the ultimate manufacturing of discrete absorbent articles in accordance with the present invention.

The term "absorbent article" herein refers to devices which absorb and contain body exudates and, more specifically, refers to devices which are placed against or in proximity to the body of the wearer to absorb and contain the various exudates discharged from the body, such as: incontinence briefs, incontinence undergarments, absorbent inserts, diaper holders and liners, feminine hygiene garments and the like. Said absorbent article may have an absorbent core having a garment surface and a body surface; a liquid permeable topsheet positioned adjacent said body surface of said absorbent core; and a liquid impermeable backsheet positioned adjacent said garment surface of said absorbent core.

The term "disposable" is used herein to describe absorbent articles which generally are not intended to be laundered or otherwise restored or reused as absorbent articles (i.e., they are intended to be discarded after a single use and, preferably, to be recycled, composted or otherwise discarded in an environmentally compatible manner).

The term "diaper" herein refers to an absorbent article generally worn by infants and incontinent persons about the lower torso.

The term "pant", as used herein, refers to disposable garments having a waist opening and leg openings designed for infant or adult wearers. A pant may be placed in position on the wearer by inserting the wearer's legs into the leg openings and sliding the pant into position about the wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the term "pant" is used herein, pants are also commonly referred to as "closed diapers", "prefastened diapers", "pull-on diapers", "training pants" and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. patent application Ser. No. 10/171,249, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

The term "machine direction (MD)" or "longitudinal" herein refers to a direction running parallel to the maximum linear dimension of the article and/or fastening material and includes directions within ±45° of the longitudinal direction.

The term "cross direction (CD)", "lateral" or "transverse" herein refers to a direction which is orthogonal to the longitudinal direction.

The term "joined" encompasses configurations whereby an element is directly secured to another element by affixing the element directly to the other element, and configurations whereby an element is indirectly secured to another element by affixing the element to intermediate member(s) which in turn are affixed to the other element.

Description

While absorbent articles are typically sold to the consumer as discrete articles packaged together, said absorbent articles are frequently manufactured from at least two continuous webs of materials. For example, FIG. 1 shows two exemplary continuous webs of materials, namely, a backsheet 13 and a topsheet 15. Said webs are unrolled and then sent through several unit operations (also known as converting). During such converting, discrete parts may be placed and joined to one or more of said webs. For instance, a first front ear 120 and a second front ear 122 may be joined interposed between backsheet 13 and topsheet 15. Said front ears will subsequently serve as attachment means during application of said absorbent article. Similarly, a first back ear 130 and a second back ear 132 may be joined to backsheet 15. Said back ears work in conjunction with said front ears to serve as attachment means during application of said absorbent article. One skilled in the art would appreciate that said ears may be joined to either or both webs in any combination and placement order. As can be seen in FIG. 1, at this stage (i.e., prior to longitudinal folding) a first longitudinal edge 116 and a second longitudinal edge 117 of said continuous web material 15 are currently positioned most longitudinally outboard from the longitudinal centerline 888. Within the region identified as absorbent article 200, a first front ear 220 and a second front ear 222 may be similarly joined. Likewise, a first back ear 230 and a second back ear 232 may be similarly joined. Lastly, a first longitudinal edge 216 and a second longitudinal edge 217 of said continuous web material 15 are currently positioned most longitudinally outboard from the longitudinal centerline 888. Within the region identified as absorbent article 300, a first front ear 320 and a second front ear 322 may be similarly joined. Likewise, a first back ear 330 and a second back ear 332 may be similarly joined. Lastly, a first longitudinal edge 316 and a second longitudinal edge 317 of said continuous web material are currently positioned longitudinally outboard from the longitudinal centerline 888.

Figure 2:
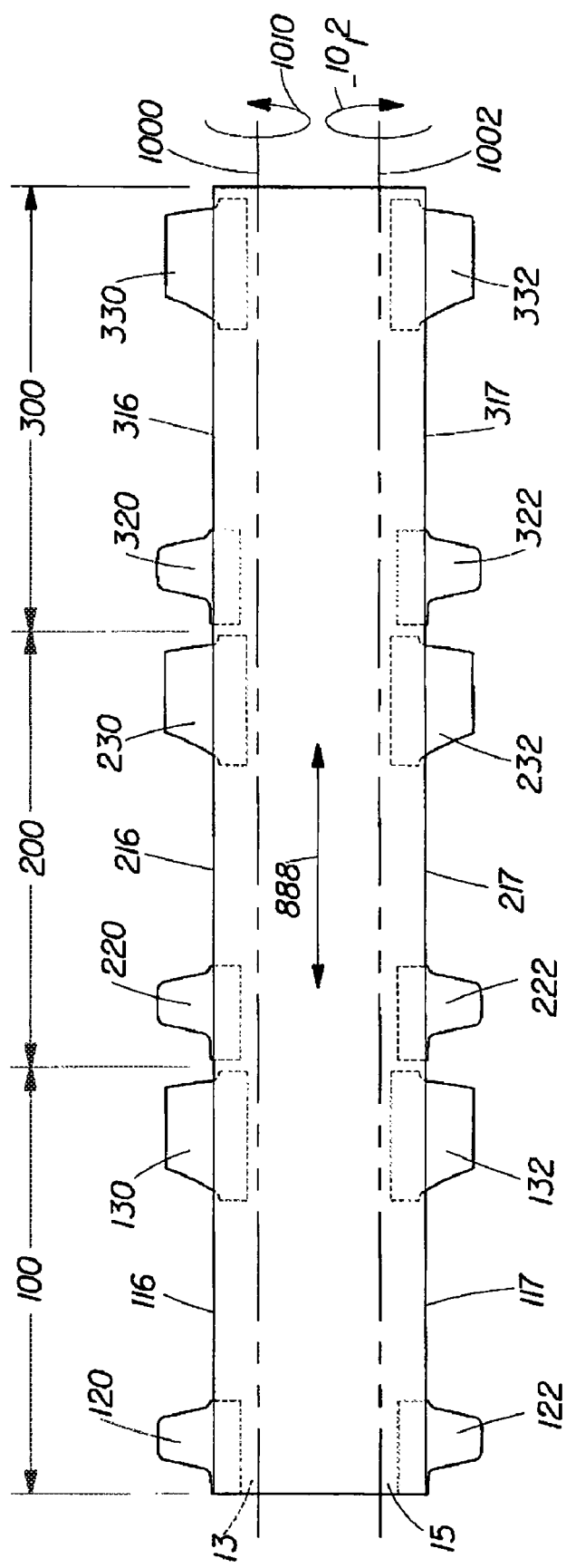
FIG. 2 is a schematic, top view of the webs from FIG. 1 with folding lines being depicted.

Once the ears are joined, said webs are folded along at least two longitudinally extending axes 1000, 1002 in directions as indicated by arrows 1010 and 1012, respectively. FIG. 2 shows said fold lines 1000 and 1002 being located longitudinally outboard of the longitudinal centerline 888 and longitudinally inboard of said first and second longitudinal edges. Said longitudinal centerline 888 extends in the MD direction.

Figure 3:
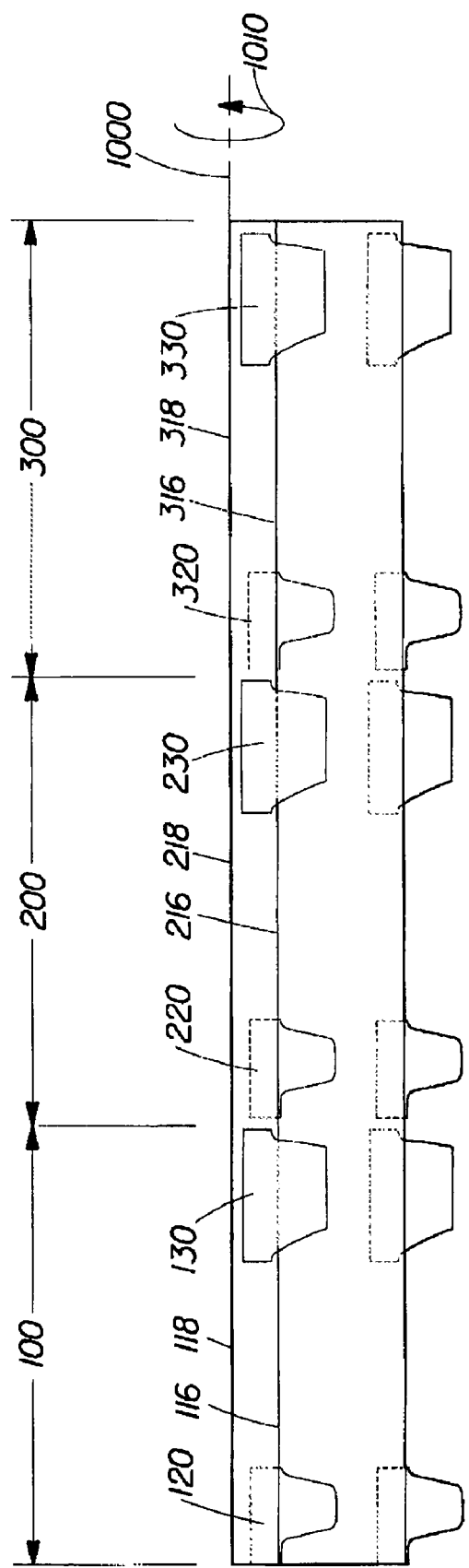
FIG. 3 is a schematic, top view of the webs from FIG. 2 with a first portion being longitudinally folded about a first fold line.

FIG. 3 shows the webs 13, 15 of FIG. 2 being folded about the first longitudinally extending axis 1000 in a direction as indicated by arrow 1010. After being folded, the first longitudinal edges 116, 216, 316 are moved longitudinally inboard. Further, a first fold edge 118 is formed within the region identified as absorbent article 100. Similarly, first fold edges 218 and 318 are formed within regions 200 and 300, respectively.

Figure 4:
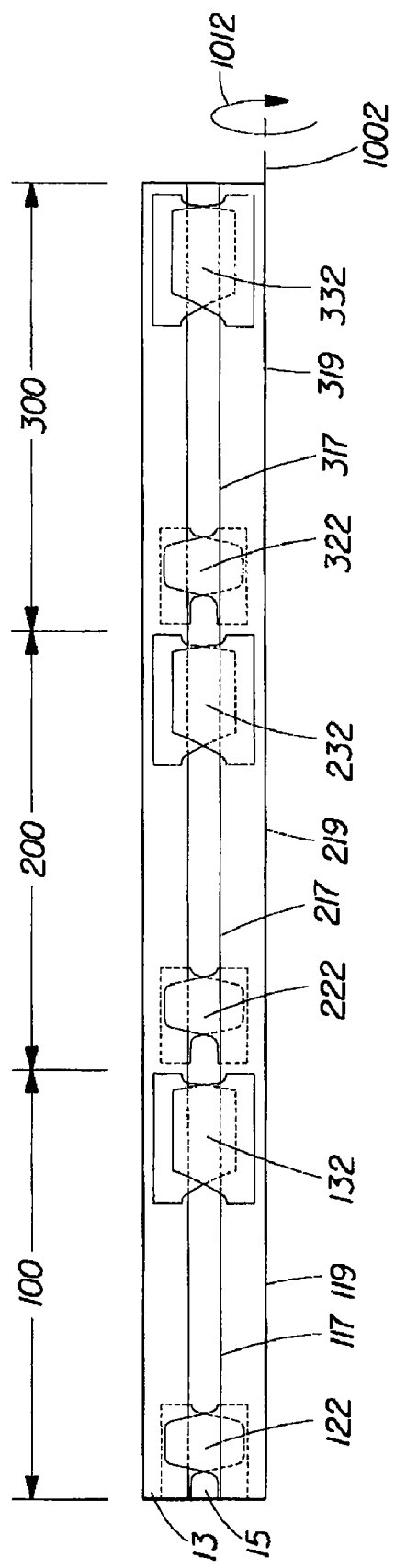
FIG. 4 is a schematic, top view of the webs from FIG. 3 with a second portion being longitudinally folded about a second fold line.

FIG. 4 shows the webs 13, 15 of FIG. 3 being folded about the second longitudinally extending axis 1002 in a direction as indicated by arrow 1012. After being folded, the second longitudinal edges 117, 217, 317 are moved longitudinally inboard. Further, a second fold edge 119 is formed within the region identified as absorbent article 100. Similarly, second fold edges 219 and 319 are formed within regions 200 and 300, respectively.

Figure 5:
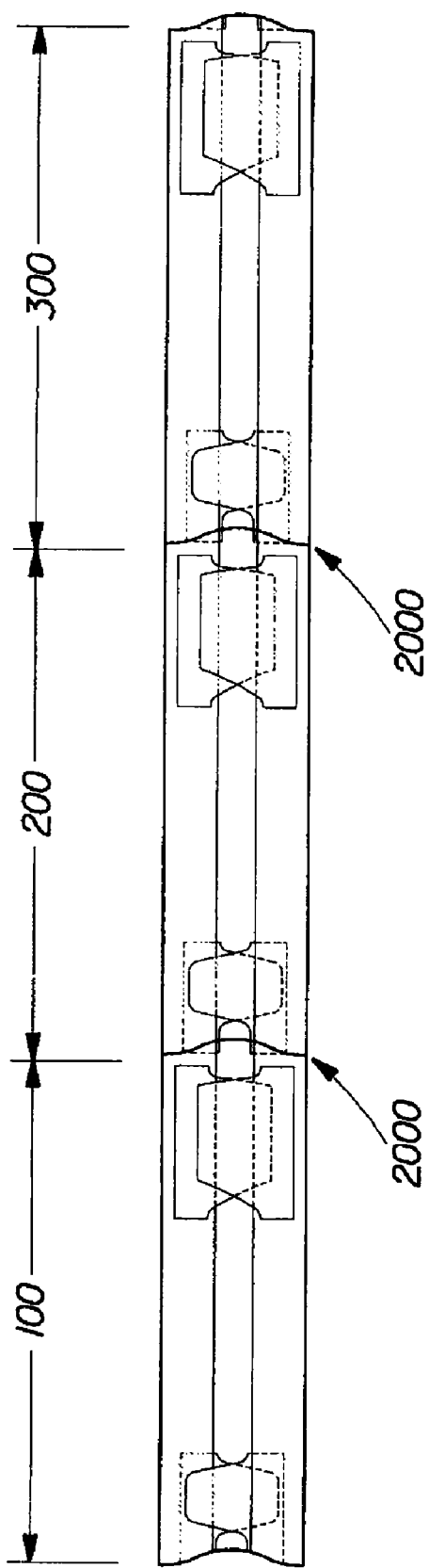
FIG. 5 is a schematic, top view of the webs from FIG. 4 with non-linear cut-lines shown.

FIG. 5 shows the webs 13, 15 of FIG. 4 being cut along cut-lines 2000. Said cut-lines 2000 may be non-linear across the longitudinal axis of said webs. The geometrical criticalities of said cut-lines 2000 will be discussed later. Said cut-lines may be a 100% severing of said webs or a less than 100% perforation of said webs. Said cut-lines may be created by any suitable technique including, but not limited to, rotary knife blade, reciprocating knife blade, air knife and laser.

Figure 6:
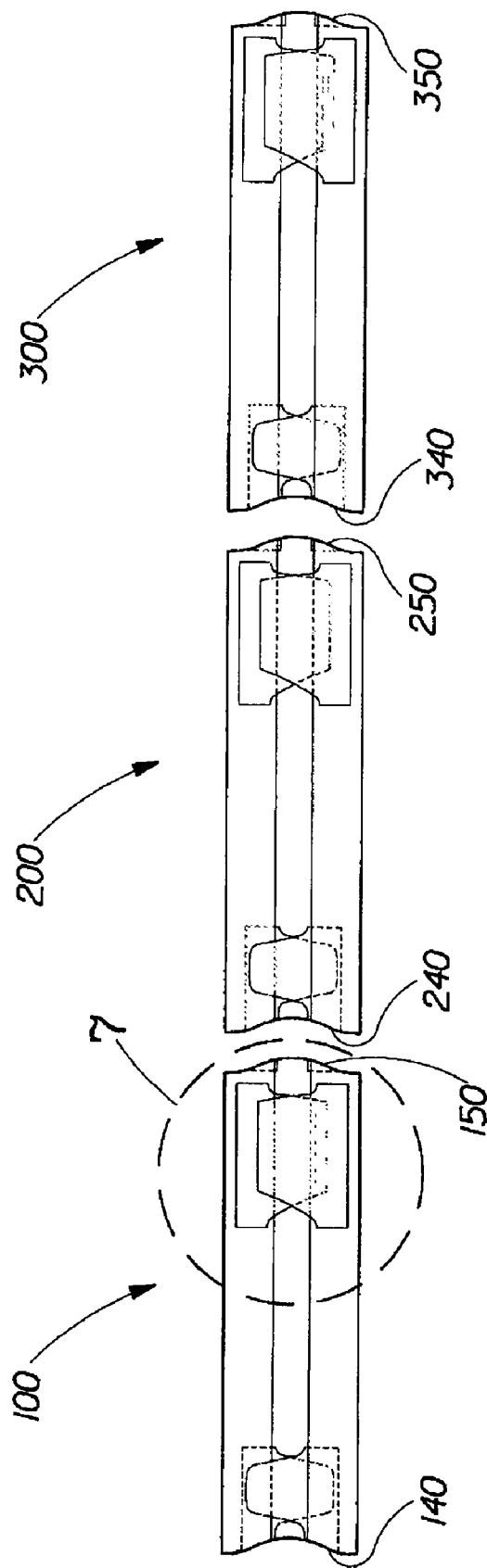
FIG. 6 is a schematic, top view of the webs from FIG. 5 being separated into individual absorbent articles.
Figure 7:
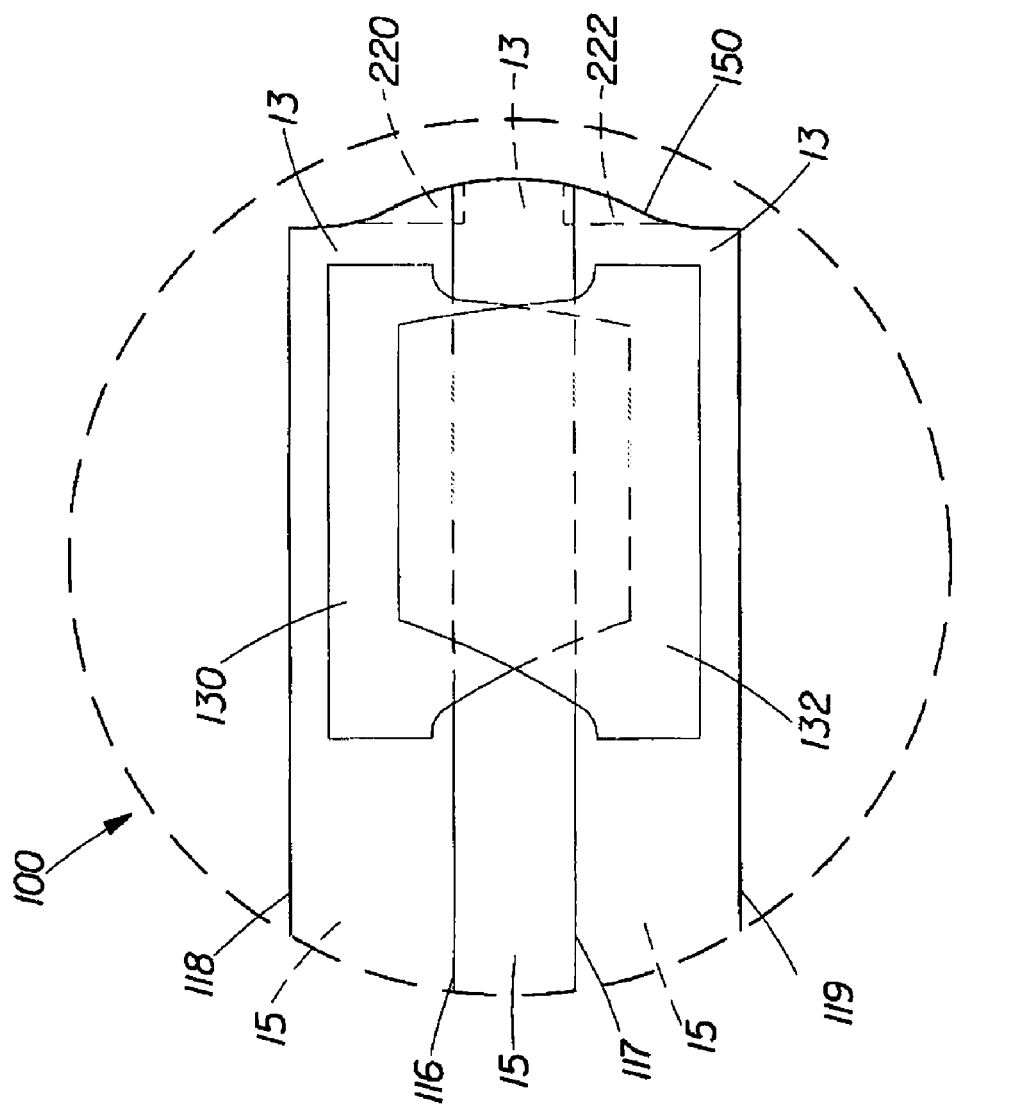
FIG. 7 is a close-up of the encircled region of FIG. 6.

FIG. 6 shows the cut webs 13, 15 of FIG. 5 being separated into discrete absorbent articles 100, 200, 300. Once separated, said discrete absorbent articles have complementary front and back end edges. For example, absorbent article 100 has a front end edge 140 and a back end edge 150. The geometries of said edges complement one another. More specifically, front end edge 140 has a U-notched portion 142 so as to provide physical clearance to the naval of the newborn wearer, while said back end edge 150 has a U-shaped protruding section 152 which positions itself up the backside of the wearer. The geometries of said edges must be complementary otherwise a scrap piece requiring removal during processing would result. FIG. 7 shows a close-up view of a region within FIG. 6 so as to provide a more detailed view of the folded and cut portion along back end edge 150.

Figure 8:
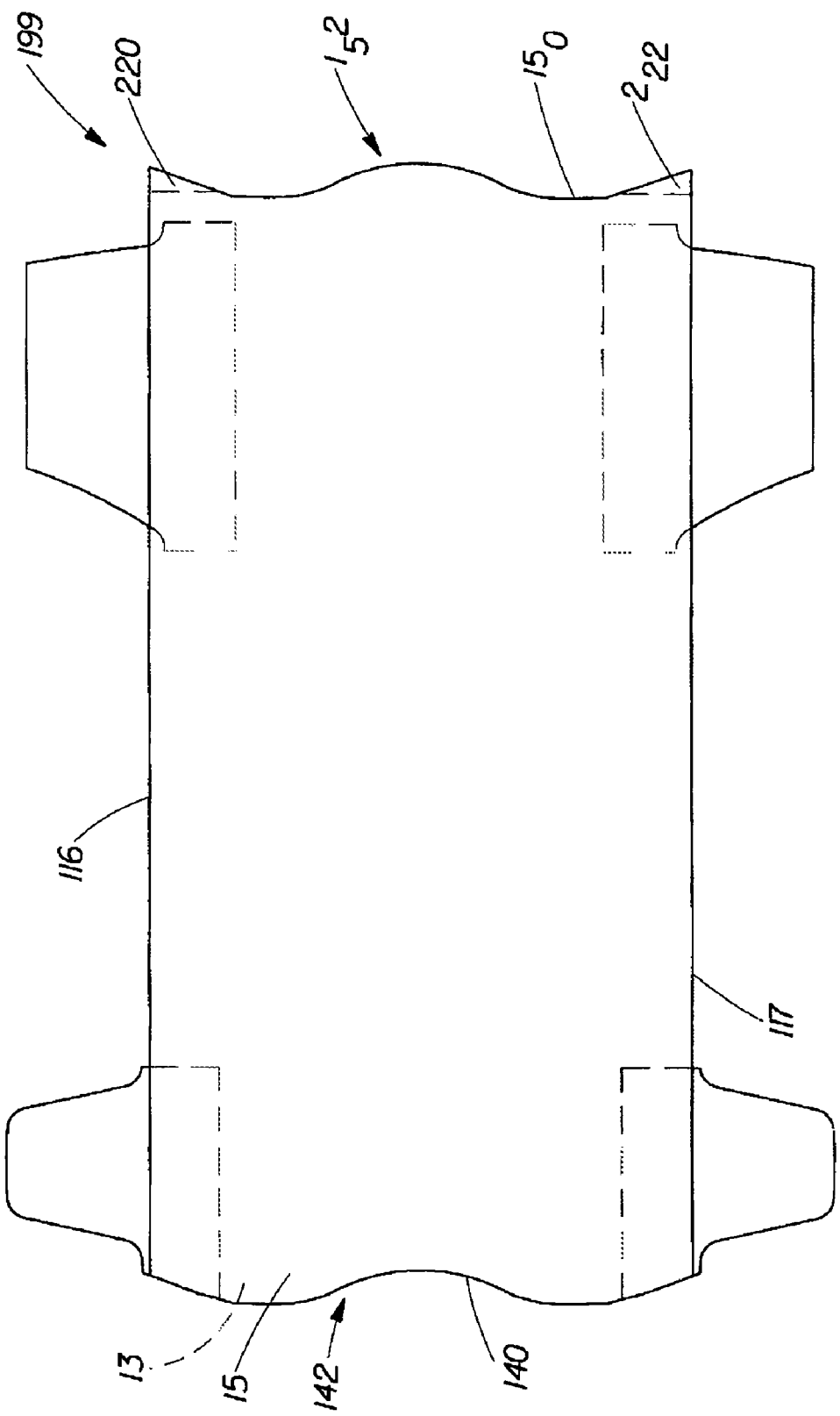
FIG. 8 is a schematic, top view of an absorbent article from FIG. 6 being unfolded.

FIG. 8 shows absorbent article 100 of FIG. 6 being unfolded similar to that of the unfolding performed by a consumer after removing said article from its packaging. In this unfolded state, first longitudinal edge 116 and second longitudinal edge 117 are now most longitudinally outboard. Along the back end edge 150, a laterally extending piece of material 199 is formed and shaped as a result of the prior fold and U-notch cut. In this exemplary novel embodiment, said laterally extending piece of material 199 is not aesthetically unpleasing nor does it present a safety concern as discussed above. So long as the u-notch cut conforms to criticalities depicted in FIG. 9, the resulting extending piece 199 will not present such a safety concern.

Figure 9:
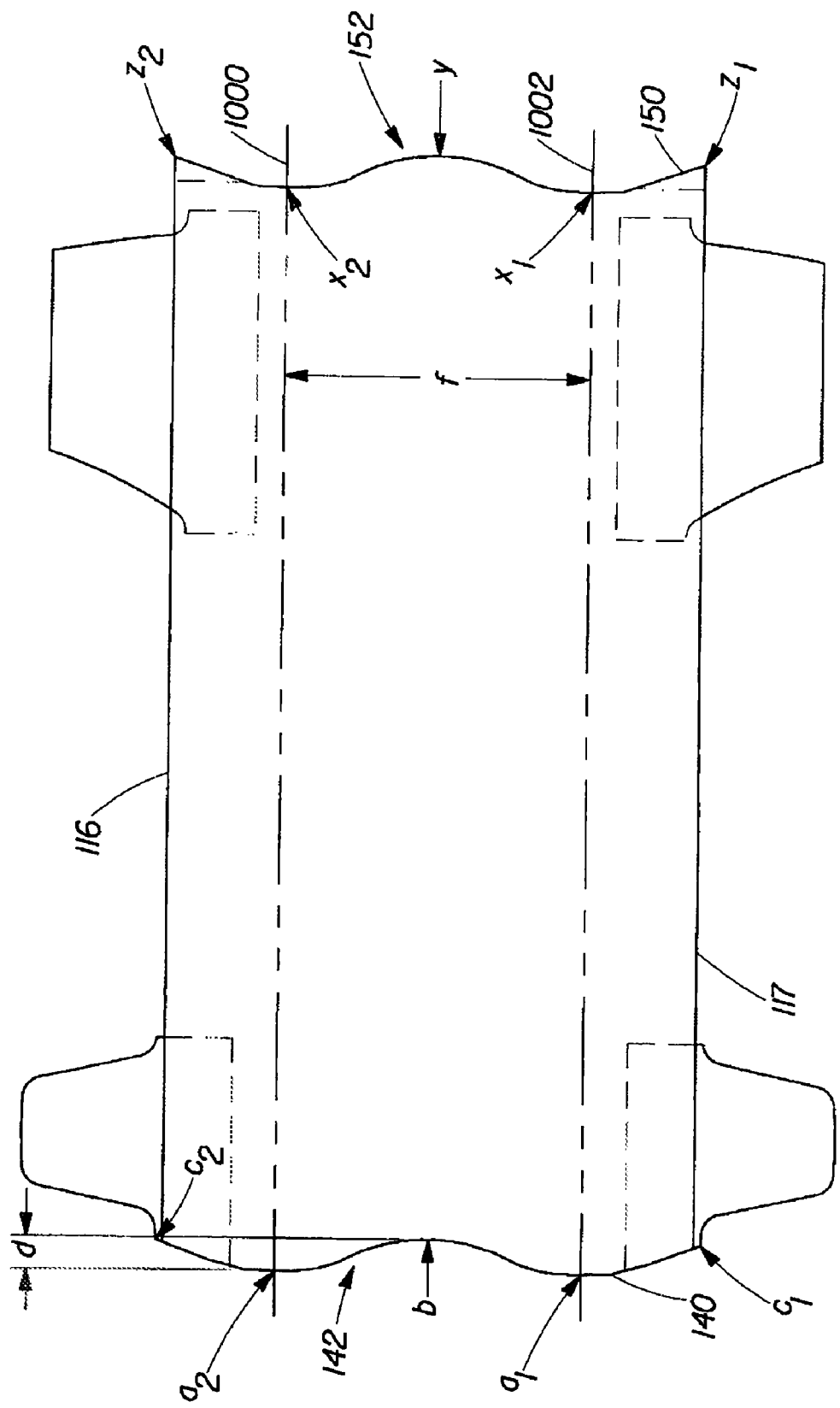
FIG. 9 is a schematic, top view of the absorbent article from FIG. 8 showing critical dimensions in accordance with the present invention.

FIG. 9 shows the unfolded absorbent article of FIG. 8 with the various critical dimensions highlighted. For example, front end edge 140 has at least three tangential points identified as $a_1$, $a_2$, and b, wherein b is longitudinally inboard of $a_1$ and $a_2$. Further, front end edge 140 has at least two edge points identified as $c_1$ and $c_2$, wherein (i) $c_1$ and $c_2$ are longitudinally inboard of $a_1$ and $a_2$ and (ii) $c_1$ and $c_2$ are longitudinally equal or outboard of b. Additionally, contour segment a-c (measured along the contour of end edge 140 between point a and point c) is a mirror image of contour segment a-b [measured along the contour of front end edge 140 between point a and point b]. Lastly, path length of contour segment a-c is less than or equal to the path length of contour segment a-b. As it relates to the complementary cut of back end edge 150, back end edge 150 has at least three tangential points identified as $x_1$, $x_2$ and y, wherein y is longitudinally outboard of $x_1$ and $x_2$. Further, back end edge 150 has at least two edge points identified as $z_1$ and $z_2$, wherein (i) $z_1$ and $z_2$ are longitudinally outboard of $x_1$ and $x_2$ and (ii) $z_1$ and $z_2$ longitudinally equal or inboard of y. Additionally, contour segment x-z (measured along the contour of back end edge 150 between point x and point z) is a mirror image to contour segment x-y [measured along the contour of back end edge 150 between point x and point y]. Lastly, path length of contour segment x-z is less than or equal to the path length of contour segment x-y. Finally, fold line 1000 may be drawn between points $a_2$ and $x_2$ and fold line 1002 may be drawn between points $a_1$ and $x_1$.

While the present invention may be appreciated as long as the above geometrical criticalities are met, it may be desirable to design a disposable diaper to have a longitudinal distance, d, between tangential point b and tangential points $a_1$, $a_2$ range from about 5 mm to about 25 mm, preferably 10 mm. Further, it may be desirable to have a lateral distance, f, between said fold lines range from about 80 mm to about 100 mm, preferably 90 mm.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

For example, one skilled in the art would appreciate that the present invention may be practiced with absorbent articles having a variety of type of fasteners. Further, the absorbent article may be an open diaper or a pant.

For example, the front ears may be moved longitudinally inboard so as not to be severed during the U-notch cut, unlike that shown the exemplary embodiment of FIGS. 5-9 wherein a portion of the front ears is severed and left sandwiched between the material layers of the preceding diaper.

What is claimed is:

1. A disposable absorbent article having a longitudinal axis and a lateral axis comprising:

a front end edge and a back end edge which, define an entire longitudinal dimension of the article, are complementary in shape, and are formed by a non-linear notch cut; said front end edge having at least three tangential points ($a_1$, $a_2$, b), wherein b is longitudinally inboard of $a_1$ and $a_2$; said front end edge having at least two edge points ($c_1$, $c_2$), wherein:

(i) $c_1$ and $c_2$ are longitudinally inboard of $a_1$ and $a_2$, and (ii) $c_1$ and $c_2$ are longitudinally equal or outboard of b;

said back end edge having at least three tangential points ($x_1$, $x_2$, y), wherein y is longitudinally outboard of $x_1$ and $x_2$; said back end edge having at least two edge points ($z_1$, $z_2$), wherein:

(i) $z_1$ and $z_2$ are longitudinally outboard of $x_1$ and $x_2$, and (ii) $z_1$ and $z_2$ are longitudinally equal or inboard of y;

said back end edge has a contour segment from said point $x_1$ to said point $z_1$ which is a mirror image of a contour segment from said point $x_1$ to said point y.

2. The disposable absorbent article according to claim 1 further comprising a longitudinal distance, d, which is measured between said tangential point b and said tangential point $a_i$, said longitudinal distance being from about 5 mm to about 25 mm.

3. The disposable absorbent article according to claim 1 further comprising a longitudinal distance, d, which is measured between said tangential point b and said tangential point $a_1$, said longitudinal distance being about 10 mm.

4. The disposable absorbent article according to claim 1 said absorbent article being longitudinally folded about a first fold line, wherein said first fold line is drawn between points $a_2$ and $x_2$, said absorbent article being longitudinally folded about a second fold line, wherein said second fold line is drawn between points $a_1$ and $x_i$, and further comprising a lateral distance, f, which is measured between said fold lines, said lateral distance being from about 80 mm to about 100 mm.

5. The disposable absorbent article according to claim 4 further comprising a lateral distance, f, which is measured between said fold lines, said lateral distance being about 90 mm.

6. The disposable absorbent article according to claim 1 wherein said absorbent article is an open diaper.

7. The disposable absorbent article according to claim 1 wherein said absorbent article is a pant.

8. The disposable absorbent article according to claim 1 further comprising an absorbent core having a garment surface and a body surface;

a liquid permeable topsheet positioned adjacent said body surface of said absorbent core;

a liquid impermeable backsheet positioned adjacent said garment surface of said absorbent core; said topsheet and backsheet together forming said front end edge and said back end edge after having been cut along a non-linear notch cut-line.

9. The disposable absorbent article according to claim 8 wherein said absorbent article is an open diaper.

10. The disposable absorbent article according to claim 8 wherein said absorbent article is a pant.

11. A disposable absorbent article having a longitudinal axis and a lateral axis comprising a front end edge and a back end edge, which define an entire longitudinal dimension of the article, are complementary in shape, and are formed by a non-linear notch cut.

* * * * *